US011285292B2

(12) United States Patent
Palmer (10) Patent No.: US 11,285,292 B2
(45) Date of Patent: *Mar. 29, 2022

(54) CLOSED SYSTEM WITH INTERMITTENT URINARY CATHETER FEED

(71) Applicant: Cure Medical LLC, Newport Beach, CA (US)

(72) Inventor: Timothy A. Palmer, Stillwater, MN (US)

(73) Assignee: Cure Medical LLC, Newport Beach, CA (US)

( * ) Notice: Subject to any disclaimer, the term of this patent is extended or adjusted under 35 U.S.C. 154(b) by 548 days.

This patent is subject to a terminal disclaimer.

(21) Appl. No.: 16/295,733

(22) Filed: Mar. 7, 2019

(65) Prior Publication Data

US 2019/0255280 A1 Aug. 22, 2019

Related U.S. Application Data

(63) Continuation-in-part of application No. 15/902,793, filed on Feb. 22, 2018, now Pat. No. 10,226,594.

(51) Int. Cl.
*A61M 27/00* (2006.01)
*A61M 25/00* (2006.01)
(Continued)

(52) U.S. Cl.
CPC ............. *A61M 25/002* (2013.01); *A61F 5/00* (2013.01); *A61F 5/4404* (2013.01);
(Continued)

(58) Field of Classification Search
CPC ............ A61M 25/0017; A61M 25/002; A61M 2025/0047; A61M 25/0111; A61M 25/013; A61M 2209/06
(Continued)

(56) References Cited

U.S. PATENT DOCUMENTS 4,451,256 A * 5/1984 Weikl ................ A61M 25/0668
604/164.03
6,053,905 A * 4/2000 Daignault, Jr. .... A61M 25/0111
206/364
(Continued)

OTHER PUBLICATIONS

Cure Medical LLC, "Instruction Guide to Sterile Self-Catheterization for Women Using the Cure Catheter® Closed System", article, pp. 1-6, http://curemedical.com/wp-content/uploads/2015/01/Sterile-SIC_women.pdf, last accessed Feb. 22, 2018.
(Continued)

*Primary Examiner* — Andrew J Mensh
(74) *Attorney, Agent, or Firm* — SoCal IP Law Group LLP; Guy Cumberbatch; Steven Sereboff (57) ABSTRACT

A sterile closed intermittent urinary catheter system which is an easier to use by virtue of ergonomic shaping to facilitate advancement and retrieval of the catheter from the collection bag. The bag may have a closed internal hole adjacent an indent in one edge that creates a narrow channel through which the catheter passes. The narrow channel is located near to and in alignment with an outlet assembly so that the catheter extends from the narrow channel directly to the outlet. A user may easily grasp the catheter from outside the bag at the narrow channel and urge the catheter forward or backward to alternately extend and retract it through the outlet. A flexible pusher sleeve with gripper features may be added around the narrow channel to further facilitate catheter advancement.

20 Claims, 4 Drawing Sheets

(51) Int. Cl.
  *A61F 5/00* (2006.01)
  *A61F 5/44* (2006.01)
  *A61M 25/01* (2006.01)

(52) U.S. Cl.
  CPC ...... *A61M 25/0113* (2013.01); *A61M 27/008* (2013.01); *A61M 25/013* (2013.01); *A61M 25/0111* (2013.01); *A61M 2027/004* (2013.01); *A61M 2202/0496* (2013.01); *A61M 2205/586* (2013.01); *A61M 2210/1096* (2013.01)

(58) Field of Classification Search
  USPC ........................................................ 604/544
  See application file for complete search history.

(56) References Cited

U.S. PATENT DOCUMENTS

| | | |
|---|---|---|
| 6,402,726 B1 | 6/2002 | Genese |
| 6,578,709 B1* | 6/2003 | Kavanagh ............ A61M 25/002 206/364 |
| 7,094,220 B2 | 8/2006 | Tonghoj et al. |
| 7,985,217 B2 | 7/2011 | Mosler et al. |
| 9,707,375 B2 | 7/2017 | Conway et al. |
| 9,782,563 B2 | 10/2017 | Palmer |
| 9,861,781 B2* | 1/2018 | Murray ................. A61F 5/4404 |
| 2007/0088330 A1 | 4/2007 | House |
| 2012/0116335 A1* | 5/2012 | Tanghoej .................. A61F 5/44 604/323 |
| 2012/0168324 A1* | 7/2012 | Carleo ................ A61M 25/002 206/210 |
| 2012/0239005 A1 | 9/2012 | Conway et al. |
| 2013/0144271 A1* | 6/2013 | Passadore ........... A61M 25/013 604/544 |

OTHER PUBLICATIONS

Cure Medical LLC, "Instruction Guide to Sterile Self-Intermittent Catheterization For Men Using the Cure Catheter® Closed System", article, pp. 1-6, http://curemedical.com/wp-content/uploads/2015/01/Sterile-SIC_men.pdf, last accessed, Feb. 22, 2018.
Cure Medical LLC, "Closed System", https://curemedical.com/cure-catheters/cure-catheter-closed-system/, last accessed Jan. 22, 2018, 13 total pages.
Health Products for You, "Coloplast Self-Cath Closed System Intermittent Catheter", https://www.healthpraductsforyou.com/p-coloplast-self-cath-straight-tip-closed-system-intermittent-catheter.html, accessed Jan. 22, 2018.

* cited by examiner

CLOSED SYSTEM WITH INTERMITTENT URINARY CATHETER FEED

RELATED APPLICATIONS

The present application is a continuation-in-part of U.S. Ser. No. 15/902,793, filed Feb. 22, 2018 under the same title, the contents of which are expressly incorporated herein.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

FIELD

The present invention relates to a closed intermittent catheter system and, more particularly, to a closed system with a shaped bag that facilitates gripping and advancement of a catheter therein.

BACKGROUND

People with neurogenic bladder disorders like spinal cord injury, spina bifida or multiple sclerosis, and non-neurogenic bladder disorders like obstruction due to prostate enlargement, urethral strictures or post-operative urinary retention, need to be continuously catheterized to empty their urinary bladders. But such continuous catheterization can lead to problems like urinary tract infections (UTI), urethral strictures or male infertility. Intermittent catheterization at regular intervals avoids such negative effects of continuous long term catheterization. Research has shown that intermittent self-catheterization helps reduce urinary tact infections, control urinary leakage (incontinence) and prevent urinary tract damage.

In our highly mobile culture, the ability to have the freedom to leave home for the day or longer is an important part of life. To accommodate this need, single use intermittent urinary catheters have been developed to allow patients to perform self-catheterization. Many intermittent catheters are designed to be inserted into the bladder while the back end is suspended over a toilet or other waste receptacle. A closed system catheter is a self-contained, sterile, pre-lubricated catheter housed within a collection bag. The collection bag eliminates the need to void the urine into a receptacle or toilet, and since it's self-contained, it eliminates the need to hook up any other kind of bag or container. The closed system is also critical for a sterile intermittent catheter insertion technique whereby the catheter is inserted without human touch.

Despite numerous products on the market, there remains a need for an easier to use sterile closed intermittent urinary catheter system.

SUMMARY OF THE INVENTION

The present application discloses a sterile closed intermittent urinary catheter system which is an easier to use by virtue of ergonomic shaping to facilitate advancement and retrieval of the catheter from the collection bag. In a preferred embodiment, a closed internal hole in the bag adjacent an indent in one edge creates a narrow channel through which the catheter passes. The narrow channel is located near to and in alignment with an outlet assembly so that the catheter extends from the narrow channel directly to the outlet. A user may easily grasp the catheter from outside the bag at the narrow channel and urge the catheter forward or backward to alternately extend and retract it through the outlet. A flexible pusher sleeve with gripper features may be added around the narrow channel to further facilitate catheter advancement.

In one embodiment, a catheter closed urinary catheter system comprises a flexible generally rectangular collection bag defining a collection volume therein. The collection bag is substantially flat when empty and has an outlet in one longitudinal end. The collection bag further has an internal through hole in its middle portion and an indent in one lateral side adjacent the through hole that creates a narrow internal channel close to and generally aligned with the outlet. An intermittent urinary catheter sealed within the collection bag has a forward end located at the outlet and an adjacent portion passing through the narrow channel of the bag so that a user may grip the catheter from outside the bag at the narrow channel and urge the catheter forward or backward to alternately extend and retract it through the outlet.

The internal through hole may be an oval shape with a long axis aligned with the narrow internal channel. A flexible sleeve may be fitted around the narrow channel and having frictional features thereon for enhanced gripping of the catheter.

Another closed urinary catheter system comprises a flexible generally rectangular collection bag defining a collection volume therein. The collection bag is substantially flat when empty and has an outlet in one longitudinal end. The collection bag further defines a narrow bridge close to and generally aligned with the outlet and having an open passage therethrough. An intermittent urinary catheter sealed within the collection bag has a forward end located at the outlet and an adjacent portion passing through the open passage defined by the narrow bridge. A flexible sleeve fits around the narrow channel and has frictional features thereon for enhanced gripping of the catheter, wherein a user may grip the catheter from outside the bag using the sleeve and urge the catheter forward or backward to alternately extend and retract it through the outlet.

In either system outlined above, the flexible sleeve is desirably silicone and is formed in an open tubular structure with two free edges; which edges may overlap. The frictional features may include grooves which define circumferential raised regions therebetween or a roughened or textured outer surface.

A feed lock may be included within the outlet of the bag of either system which allows free forward passage of the catheter out of the bag but hinders retraction of the catheter. Preferably, the outlet comprises a relatively rigid gripping hub through which the catheter passes. Further, an introducer tip may extend from an outer end of the outlet through which the catheter passes, with a sterile cap secured over the introducer tip. Finally, a gel reservoir may be secured within the hub that lubricates the catheter as it passes through the reservoir.

DETAILED DESCRIPTION OF A PREFERRED EMBODIMENT

The present application provides a sterile closed intermittent urinary catheter system which is an easier to use by virtue of ergonomic shaping to facilitate advancement and retrieval of the catheter from the collection bag. The catheter is advanced by hand through manipulation from outside the bag.

Figure 1:
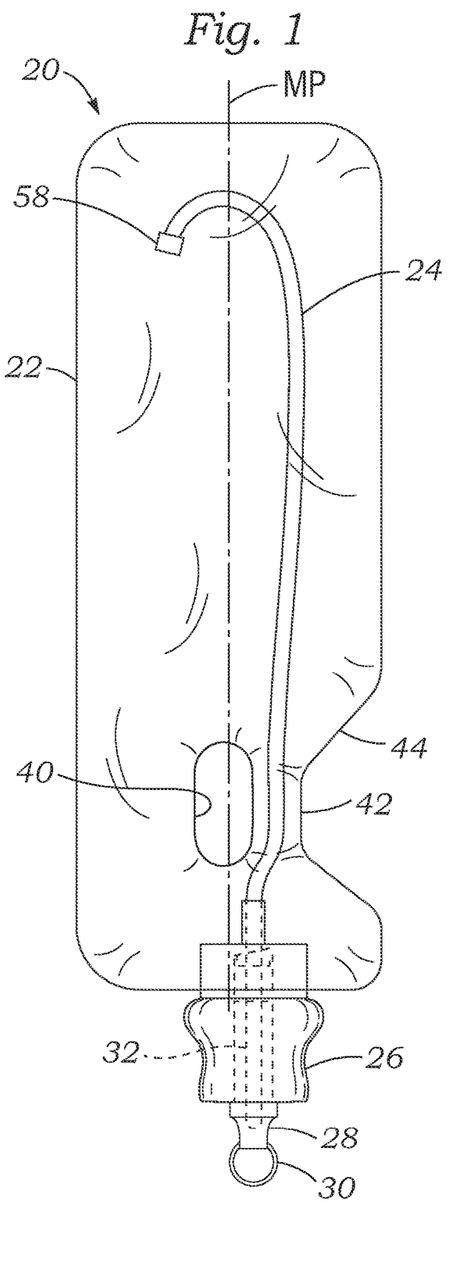
FIG. 1 is a front view of an exemplary sterile closed intermittent urinary catheter system having a narrow channel formed in a collection bag to facilitate feeding of a catheter therefrom.
Figure 2:
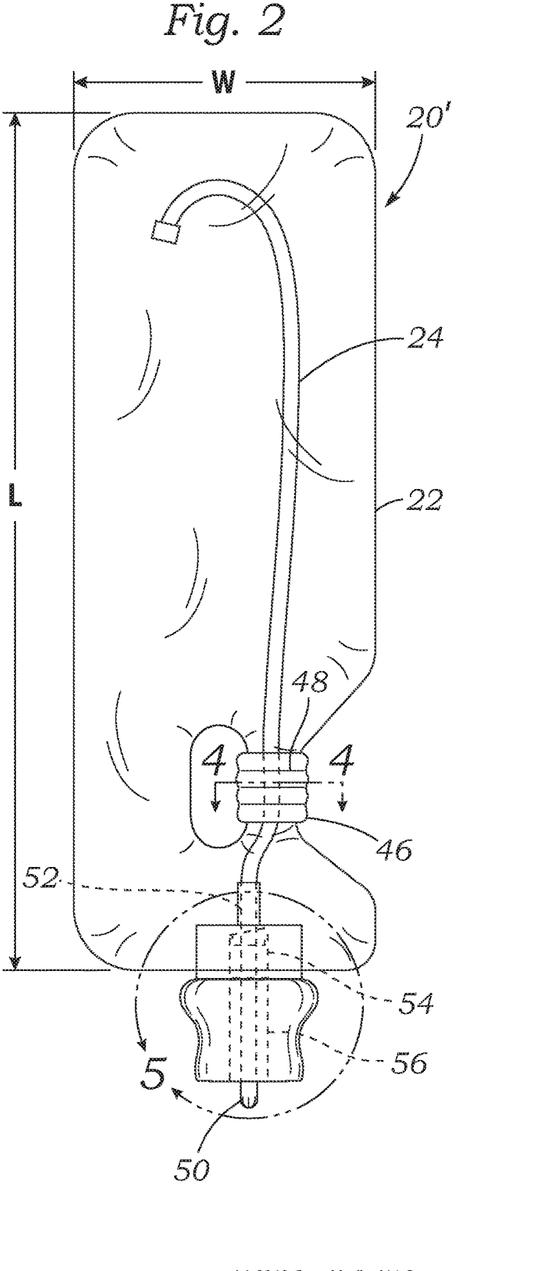
FIG. 2 is a front view of an alternative sterile closed intermittent urinary catheter system similar to that shown in FIG. 1 with an ergonomic sleeve positioned around the narrow channel to further facilitate feeding of a catheter therefrom.

FIG. 1 is a front view of an exemplary sterile closed intermittent urinary catheter system 20 having a flexible, preferably transparent, collection bag 22 with a generally rectangular profile and defining a collection volume therein. The shape has a length dimension L between longitudinal ends and a width dimension W between lateral sides, as shown in FIG. 2. An intermittent catheter 24 is stored in the bag, and may be 14 or 16 inches in length. The collection bag 22 is generally shorter in length than the catheter 24 so that the catheter is curled or coiled therein. In one embodiment, the length dimension L is about 415-425 mm, and the width dimension W is about 125-135 mm, or in other words the bag 22 is roughly 3-4 times longer than it is wide.

The collection bag 22 has an outlet at one longitudinal end including an outlet hub 26. The bag 22 is formed of a suitable flexible polymer such as polyethylene, while the hub 26 is a rigid polymer and has a larger and easy-to-grip external shape as shown. The bag 22 is desirably formed by heat-sealing or otherwise affixing peripheral edges of two faces or panels together, as well as around the hub 26, in a manner which ensures sterility of the internal collection volume or cavity thus formed. Preferably, the two panels are identical (matching). Securing the two faces together at their edges thus results in a relatively flat, 2D bag when empty, though of course the bag expands to a 3D shape when the collection volume fills with urine.

A sterile closure 28 affixes over an outlet opening (not shown) in the hub 26 and may be provided with a grip, handle or ring such as shown at 30 for easy removal. A distal tip 32 of the catheter is seen in phantom located within the hub 26, just inside the outlet opening, which is its shipped position prior to use.

The collection bag 22 also has an internal through hole 40 (internal meaning closed to the outer edges of the bag) defined by inner edges of the bag material secured together in an oval shape such as by heat sealing. The through hole 40 terminates near to the longitudinal outlet end of the bag 22, preferably within an inch or two, and may be centered (or approximately centered) along midplane MP of the width dimension W of bag. A narrow bridge 42 is formed in the collection bag 22 by the through hole 40 and an adjacent seam formed by the two matching panels sealed together; in this embodiment an indented section 44 in one lateral side of the bag 22. The faces of the bag 22 are not attached to each other along the bridge 42 so that a narrow open channel or passage in the collection volume is thus formed. The oval internal through hole 40 has a long axis aligned with the narrow internal channel. The indented section 44 may comprise a generally trapezoidal indent as shown, or may be more rectangular or more rounded, as desired. The catheter 24 passes through the narrow channel formed in the bridge 42 which facilitates feeding of the catheter from the bag 22, as will be described. First, a complete description of the preferred system components is helpful.

Figure 1A:
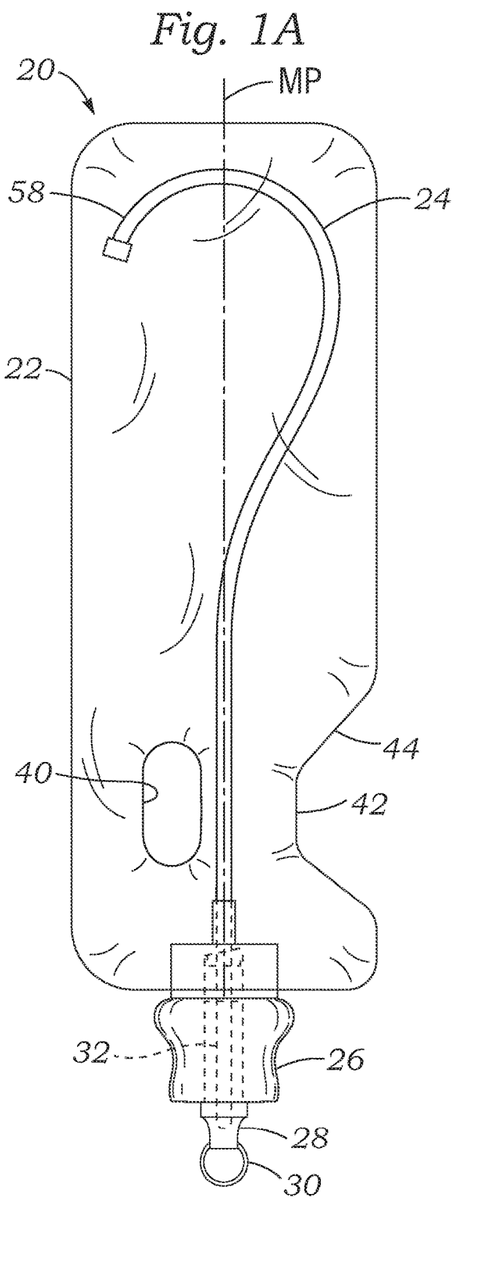
FIG. 1A is a front view of a catheter system similar to FIG. 1 with a through hole moved to permit alignment of the catheter with an outlet assembly.

FIG. 1A is a front view of a catheter system similar to FIG. 1 with the through hole 40 moved farther away from the indented section 44 to permit longitudinal alignment of the narrow open channel or passage and catheter 24 with the outlet hub 26. The through hole 40 is still adjacent the midplane MP, and the outlet hub 26 is now centered along the midplane MP. Aligning the catheter 24 with the outlet hub 26 in this manner facilitates movement of the catheter out of the collection bag 22 by reducing any frictional impediment from misalignment or bending of the catheter through the narrow channel. In all other respects, the collection bag 22 is the same as described above so that like elements are given like part numbers.

Figure 1B:
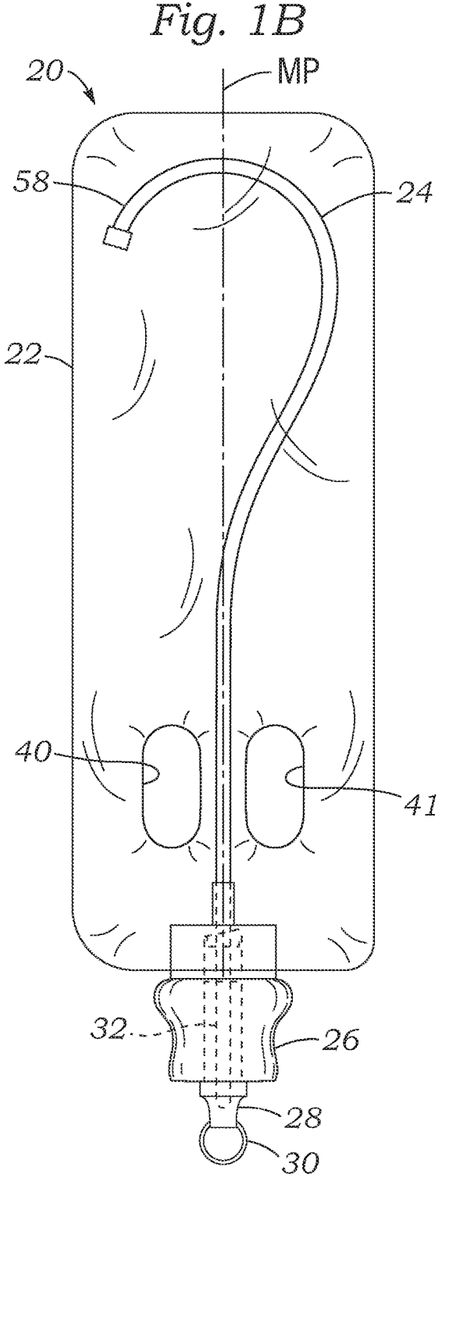
FIG. 1B is a front view of a catheter system similar to FIG. 1 with two through holes flanking a centered channel through which the catheter passes.

FIG. 1B is a front view of a catheter system similar to FIG. 1 with two through holes 40, 41 flanking the bridge 42 to form the narrow open channel or passage in the collection volume along the midplane MP. The outlet hub 26 is again centered along the midplane MP. In this embodiment there is no indented section 44 in one lateral side wall, both lateral side walls are straight. Instead, the two through holes 40, 41 both form seams between the matching panels, and the two closest or adjacent seams define the narrow bridge 42 and channel. Desirably, the two through holes 40, 41 are identical and spaced equidistantly across the longitudinally-extending midplane M of the collection bag. The through holes 40, 41 also provide handles of sorts for the user to manipulate the collection bag 22. In all other respects, the collection bag 22 is the same as described above so that like elements are given like part numbers.

FIG. 2 is a front view of an alternative sterile closed intermittent urinary catheter system 20' similar to that shown in FIG. 1. The only change from the system 20 in FIG. 1 is the addition of an ergonomic pusher sleeve 46 having grooves 48 positioned around the narrow bridge 42 to further facilitate feeding of the catheter 24 from the bag 22.

FIG. 2 shows the closure 28 removed from the hub 26 to expose an introducer tip 50. The distal tip 32 of the catheter preferably resides just inside the introducer tip 50 when packaged. Internal components of the outlet end of the bag 22 are shown exploded in FIG. 5 and include a rigid sleeve 52 through which the catheter 24 passes, a catheter feed lock 54, and a lubricating gel reservoir 56. Prior to exiting the bag 22, the catheter passes through all three of these components. It should be noted that rather than providing the lubricating gel reservoir 56, the catheter 24 may be pre-lubricated along its length, or may be provided with a dry hydrophilic coating which, when wetted, becomes lubricious. In the latter case, a small sachet of water is provided within the bag 22 which, when ruptured, wets the catheter 24.

Figure 3A:
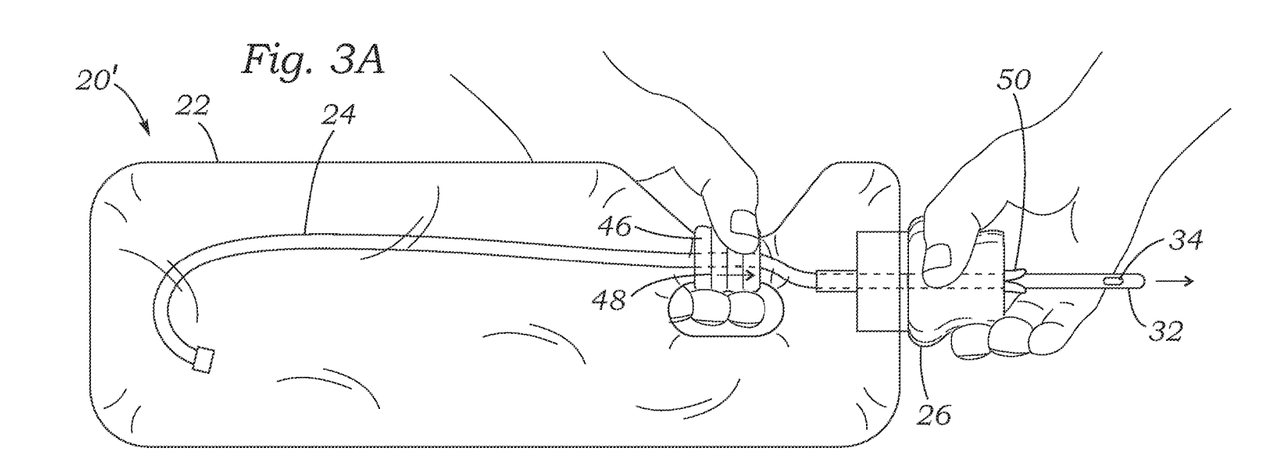
FIGS. 3A and 3B are front views of the system of FIG. 2 illustrating two stages in the use thereof.
Figure 3B:
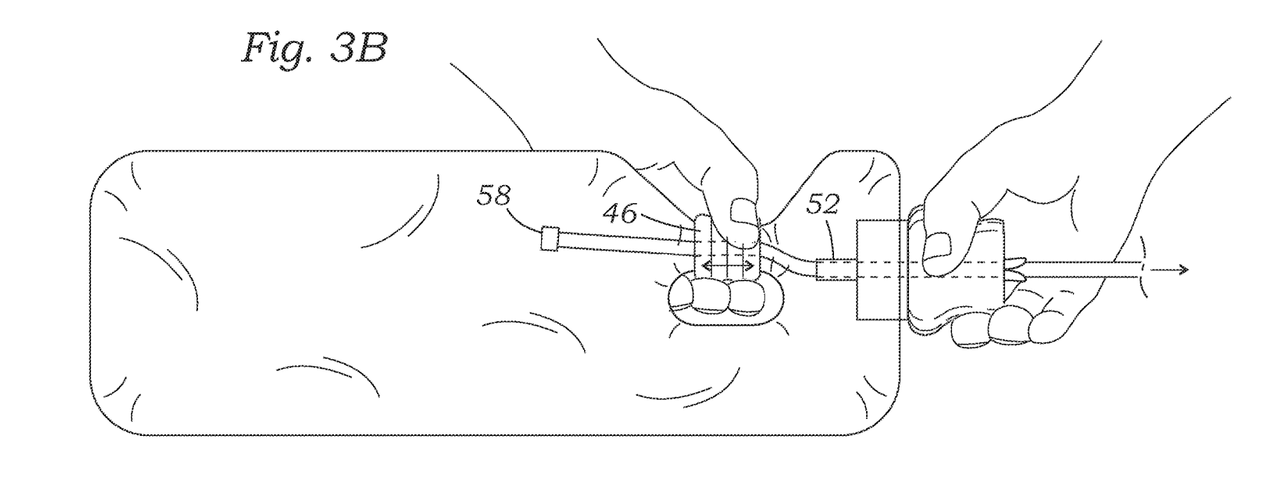

FIGS. 3A and 3B are front views of the system 20' of FIG. 2 illustrating two stages in the use thereof. After removal of the outlet closure 28 and prior to longitudinal advancement of the catheter 24 from the bag 22, the user inserts the introducer tip 50 into the urethra (men or women). The user then advances the catheter 24 forward, as indicated by the arrow, by pinching it with the relatively flexible pusher sleeve 46 through the bag 22 and urging it forward while holding the outlet hub 26 steady. The introducer tip 50 is made of a flexible elastomer which has petals that the catheter tip 32 spreads apart upon passage therethrough. The introducer tip 50 helps prevent any bacteria that may be around the urethra opening from contacting the catheter tip 32, which in turn helps reduce instances of infection. The user continues to slowly push the catheter 24 through the introducer tip 50 and into the urethra until the catheter reaches the bladder and urine begins to flow. The catheter 24 has one or more small eyelets 34 at its distal tip 32 into which the urine flows. The lubricated nature of the catheter 24 eases the insertion.

When fully inserted, the system 20' may be in the configuration shown in FIG. 3B with the catheter 24 nearly fully extended out of the bag 22. The double-headed arrow shown on the pusher sleeve 46 indicates the ability to adjust the final longitudinal position of the catheter 24. An enlarged collar 58 attached to a rear end of the catheter 24 is sized so as to be unable to pass through the rigid sleeve 52 on the inner end of the outlet assembly which serves as a safety measure to prevent full extraction of the catheter 24 from the bag 22.

The pusher sleeve 46 acts as a grip of sorts around the catheter 24 within the bag. The pusher sleeve 46 is desirably made of a soft elastomer so that it may be easily squeezed and deform around the catheter 24. In the configuration shown, the sleeve 46 desirably has circumferential grooves that create circumferential raised regions therebetween which enhance the friction between the user's hand and the sleeve. Of course, other means of doing the same thing are contemplated, such as a roughened or textured outer surface, bumps, extremely soft foam, etc.

Furthermore, it should be noted that the sleeve 46 is added merely to enhance the grip of the user on the catheter 24, but that it is the shape of the collection bag 24 in the first place that facilitates catheter advancement. In particular, passage of the catheter 24 through the narrow channel formed in the bridge 42 seen in FIG. 1 close to the outlet end of the bag is the main improvement. With reference back to FIG. 1, the channel formed in the bridge 42 is generally aligned with the central axis of the outlet hub 26 and its components, so that the catheter 24 can easily be advanced from the bag 22 by gripping it at the channel and urging it forward relative to the hub. Although bags without the through hole 40, bridge 42 and indent 44 are available and the general process of advancing a catheter therefrom is the same (gripping the catheter through the bag), certain difficulties arise. First, the user may grip the catheter too far from the outlet, which may cause the catheter to bend and reduces pushing force. Second, the user may not push the catheter 24 in alignment with the outlet, which also reduces leverage. Finally, the mere task of gripping the catheter between two generally flat bag panels may not be easy, especially for those with dexterity challenges. The narrow bridge 42 located close to and in alignment with the outlet hub 26 greatly reduces these potential hindrances, and may be a big improvement for some users.

Figure 4A:
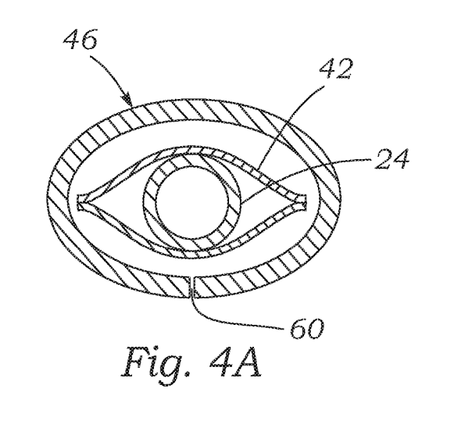
FIG. 4A is a sectional view taken along line 4-4 in FIG. 2 showing one embodiment of the ergonomic sleeve.
Figure 4B:
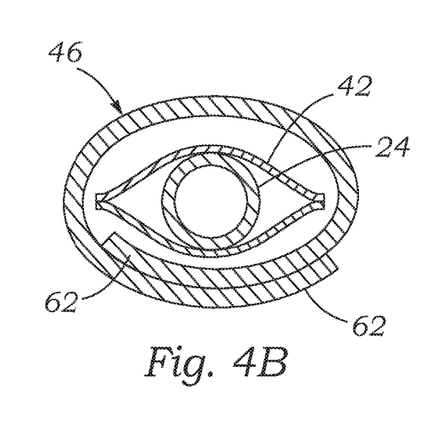
FIG. 4B is a similar view showing an alternative ergonomic sleeve.

The pusher sleeve 46 is preferably a loose part that fits around the narrow bridge 42, though it may also be adhered thereto. Since the sleeve 46 passes through the closed through hole 40, it cannot prior to assembly on the bag 22 be formed as a closed tube. There are several solutions in this regard. FIG. 4A is a sectional view taken along line 4-4 in FIG. 2 showing one embodiment of the ergonomic pusher sleeve 46. The sleeve 46 may be formed in generally an oval tube with two abutting free edges coming together at 60. The tube of the sleeve 46 fits closely around the lenticular-shaped portion of the bag 22 that forms the bridge 42, with the catheter 24 shown therein. FIG. 4B is an alternative ergonomic sleeve 46 which also defines an oval-shaped tube with two somewhat overlapping free edges 62. Of course, variations of these configurations are well within the level of skill in the art.

Figure 5:
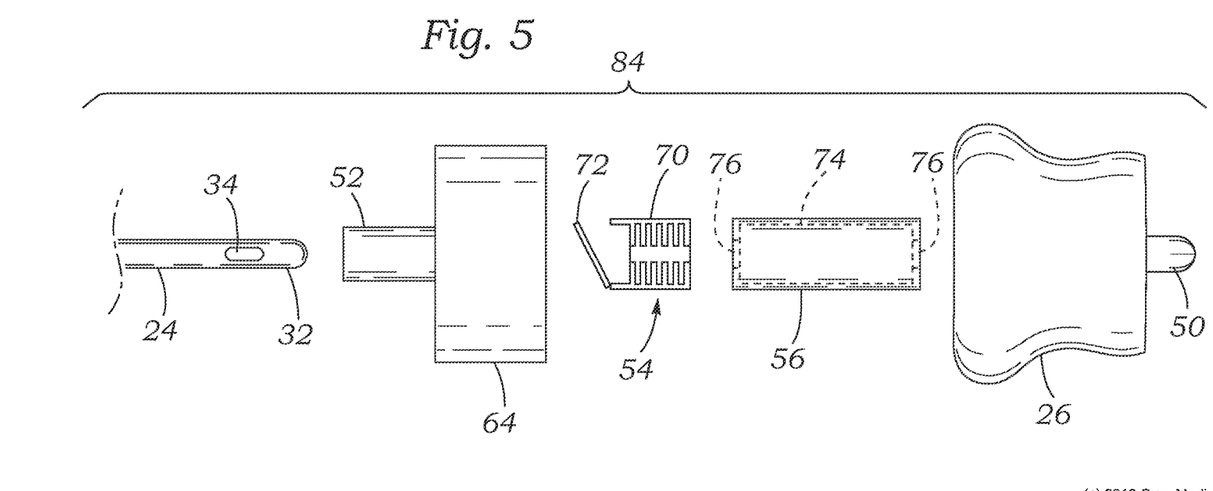
FIG. 5 is an exploded view of exemplary components provided at an outlet of the closed intermittent urinary catheter systems disclosed herein.

Finally, FIG. 5 shows a few more details of the components at the outlet of the closed systems 20 disclosed herein. First, a generally cylindrical rigid housing 64 may attach to the inner end of the hub 26 and provide a cavity therein for the feed lock 54. The feed lock 54 functions to permit one-way forward advancement of the catheter 24, but inhibits rearward movement thereof. In one embodiment, a cylindrical housing with a throughbore provides support for a thin flap 72 that attaches to the housing via a living hinge. Although not shown, the flap 72 has a throughbore as well and receives the tubular catheter 24 therethrough. When the catheter 24 advances forward, the flap 72 is pushed to an orientation perpendicular to the longitudinal direction, which eases passage of the catheter through its therethrough. Conversely, when the catheter 24 is displaced rearward, the flap 72 assumes the angled orientation shown which tends to resist movement of the catheter by virtue of the now-angled throughbore. A latch may be provided to enable a user to fix the flap 72 against the housing 70 to permit retraction of the catheter 24. Similar devices are disclosed in co-pending U.S. patent application Ser. No. 15/671,341, the contents of which are hereby expressly incorporated by reference.

FIG. 5 also illustrates an internal chamber 74 of the lubricating gel reservoir 56 which resides between two end openings 76 sized slightly larger than the tubular catheter 24. As seen in FIG. 1, the distal tip 32 of the catheter 24 preferably sits within the lubricating medium in the chamber 74 prior to use. Of course, other reservoirs are contemplated, such as the resilient reservoirs disclosed in U.S. Pat. No. 9,833,592, the contents of which are hereby expressly incorporated by reference.

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. Acts, elements and features discussed only in connection with one embodiment are not intended to be excluded from a similar role in other embodiments.

It is claimed:

1. A closed urinary catheter system comprising:
   a flexible collection bag with a longitudinal dimension, a
      shorter lateral dimension and a longitudinally-extending midplane, the collection bag having an inner cavity defining a collection volume therein, the collection bag having two flexible matching panels sealed together at outer edges and having an outlet formed in one longitudinal end, the collection bag further having an internal through hole defined by inner edges of the matching panels sealed together and an indent in one lateral outer edge of the collection bag co-extensive with the through hole such that a portion of the bag between the through hole and the indent creates a narrow internal channel within the inner cavity; and an intermittent urinary catheter located within the inner cavity having a forward end located at the outlet and an adjacent portion passing through the narrow internal channel of the collection bag directly in between the matching panels so that a user may grip the catheter from outside the bag at the narrow internal channel and urge the catheter forward or backward to alternately extend and retract it through the outlet.

2. The system of claim 1, wherein the through hole is an oval shape with a long axis aligned with the internal channel.

3. The system of claim 1, wherein the midplane of the collection bag intersects the through hole.

4. The system of claim 1, further including a flexible sleeve outside the bag fitted around the portion of the bag forming the narrow internal channel and having frictional features thereon for enhanced gripping of the catheter.

5. The system of claim 4, wherein the flexible sleeve is silicone and is formed in an open tubular structure with two free edges that overlap.

6. The system of claim 1, wherein the narrow internal channel of the collection bag is longitudinally aligned with the outlet so that the catheter is longitudinally oriented through the narrow internal channel to the outlet.

7. The system of claim 1, wherein the indent is trapezoidal in shape.

8. The system of claim 1, further including a feed lock within the outlet which allows free forward passage of the catheter out of the bag but hinders retraction of the catheter.

9. The system of claim 1, wherein the outlet comprises a rigid gripping hub through which the catheter passes.

10. The system of claim 9, further including an introducer tip extending from an outer end of the gripping hub and through which the catheter passes, and a sterile cap secured over the introducer tip.

11. The system of claim 9, further including a gel reservoir secured within the gripping hub that lubricates the catheter as it passes through the reservoir.

12. A closed urinary catheter system comprising: a flexible collection bag elongated in one dimension with two flexible matching panels sealed together at outer edges forming an inner cavity that defines a collection volume therein, the collection bag having an outlet formed in one longitudinal end, the collection bag further having an internal through hole defined by inner edges of the matching panels sealed together, the through hole being elongated in the same direction as the collection bag so as to create an elongated narrow bridge in the matching panels between the through hole and an adjacent seam formed by lateral outer edges of the two matching panels sealed together and defining an indent, so as to form a narrow internal channel open to the inner cavity between the through hole and the indent; and an intermittent urinary catheter located within the inner cavity having a forward end located at the outlet and an adjacent portion passing through the narrow internal channel of the collection bag directly in between the matching panels so that a user may grip the catheter from outside the bag at the narrow internal channel and urge the catheter forward or backward to alternately extend and retract it through the outlet.

13. The system of claim 12, further including a flexible sleeve fitted around the narrow bridge and having frictional features thereon for enhanced gripping of the catheter, wherein a user may grip the catheter from outside the bag using the sleeve and urge the catheter forward or backward to alternately extend and retract it through the outlet.

14. The system of claim 12, wherein the narrow internal channel of the collection bag is longitudinally aligned with the outlet so that the catheter is longitudinally oriented through the narrow internal channel to the outlet.

15. The system of claim 12, wherein the adjacent seam is formed by a second through hole elongated in the same direction as the collection bag, the two through holes being identical and spaced equidistantly across a longitudinally-extending midplane of the collection bag.

16. The system of claim 12, wherein the collection bag has a longitudinal dimension, a shorter lateral dimension and a longitudinally-extending midplane, the through hole being elongated in the longitudinal direction and the midplane intersects the through hole, and wherein the adjacent seam is formed by a lateral outer edge of the collection bag defining the indent which is co-extensive with the through hole that creates the elongated narrow bridge with the through hole.

17. The system of claim 12, further including a feed lock within the outlet which allows free forward passage of the catheter out of the bag but hinders retraction of the catheter.

18. The system of claim 12, wherein the outlet comprises a rigid gripping hub through which the catheter passes.

19. The system of claim 18, further including an introducer tip extending from an outer end of the gripping hub and through which the catheter passes, and a sterile cap secured over the introducer tip.

20. The system of claim 18, further including a gel reservoir secured within the gripping hub that lubricates the catheter as it passes through the reservoir.

* * * * *

UNITED STATES PATENT AND TRADEMARK OFFICE
CERTIFICATE OF CORRECTION

| | |
|---|---|
| PATENT NO. | : 11,285,292 B2 |
| APPLICATION NO. | : 16/295733 |
| DATED | : March 29, 2022 |
| INVENTOR(S) | : Timothy A. Palmer |

It is certified that error appears in the above-identified patent and that said Letters Patent is hereby corrected as shown below:

In the Specification

Column 1, Line 42: replace "tact" with --tract--.

Signed and Sealed this
Seventh Day of June, 2022

*Katherine Kelly Vidal*

Katherine Kelly Vidal
*Director of the United States Patent and Trademark Office*